United States Patent
Sakamoto et al.

(10) Patent No.: US 8,701,512 B2
(45) Date of Patent: Apr. 22, 2014

(54) CELL FOR TESTING MICROBEADS AND METHOD OF ANALYZING MICROBEADS

(75) Inventors: Naohisa Sakamoto, Tokyo (JP); Noriyuki Kishii, Kanagawa (JP); Kazumine Ito, Tokyo (JP)

(73) Assignee: Sony Corporation, Tokyo (JP)

( * ) Notice: Subject to any disclaimer, the term of this patent is extended or adjusted under 35 U.S.C. 154(b) by 660 days.

(21) Appl. No.: 12/965,420

(22) Filed: Dec. 10, 2010

(65) Prior Publication Data

US 2011/0138890 A1    Jun. 16, 2011

(30) Foreign Application Priority Data

Dec. 16, 2009 (JP) ................................ P2009-284726
Jul. 7, 2010 (JP) ................................ P2010-154877

(51) Int. Cl.
*B01L 3/00* (2006.01)
*G01N 15/14* (2006.01)
*G01N 33/58* (2006.01)

(52) U.S. Cl.
CPC ..... *B01L 3/502761* (2013.01); *B01L 3/502753* (2013.01); *G01N 15/1463* (2013.01); *G01N 33/582* (2013.01); *B01L 2200/0668* (2013.01); *B01L 2300/0877* (2013.01); *B01L 2400/0487* (2013.01)
USPC ............. 73/866; 73/61.75; 250/576; 356/426

(58) Field of Classification Search
CPC .................... B01L 3/502753; B01L 3/502761; B01L 2200/0668; B01L 2300/0877; B01L 2400/0487; G01N 15/1463; G01N 33/582
USPC ................. 73/38, 61.75, 866; 250/252.1, 576; 356/243.2, 335, 426–427
See application file for complete search history.

(56) References Cited

U.S. PATENT DOCUMENTS 3,608,357 A * 9/1971 Meunier ............................ 73/38
6,432,290 B1 * 8/2002 Harrison et al. B01L 2200/0668
(Continued)

FOREIGN PATENT DOCUMENTS

JP     2005-504275     2/2005
JP     2009-270946     2/2008
(Continued)

OTHER PUBLICATIONS

"Pillar array microtraps with negative dielectrophoresis.", Cui Hai-Hang et al., Langmuir: The ACS Journal of Surfaces and Colloids Apr. 9, 2009 LINKD—PUBMED:19708133, vol. 25, No. 6, Apr. 9, 2009, pp. 3336-3339, XP002627288, ISSN: 0743-7463.

(Continued)

*Primary Examiner* — Thomas P Noland
(74) *Attorney, Agent, or Firm* — K&L Gates LLP

(57) ABSTRACT

Disclosed herein is a cell for testing microbeads, used for testing microbeads each formed in a cylindrical shape having an upper surface and a lower surface opposite to and substantially parallel to each other and a side surface continuous with the upper and lower surfaces, at least one of the upper surface and the lower surface being provided with an identification pattern, the cell including: a support substrate; and a cover disposed opposite to the support substrate, wherein a space between the support substrate and the cover forms a containing space in which to dispose the microbeads, and the distance between the support substrate and the cover is greater than the thickness of the microbeads and smaller than twice the thickness of the microbeads.

9 Claims, 7 Drawing Sheets

(56) References Cited

U.S. PATENT DOCUMENTS

| | | | |
|---|---|---|---|
| 6,767,733 B1* | 7/2004 | Green | B01L 2400/0487 |
| 7,141,378 B2* | 11/2006 | Miller et al. | G01N 33/582 |
| 2003/0027187 A1* | 2/2003 | Strick et al. | 435/6 |
| 2003/0091475 A1* | 5/2003 | Yu et al. | B01L 3/502761 |
| 2004/0132122 A1* | 7/2004 | Banerjee et al. | 435/7.92 |
| 2004/0235014 A1* | 11/2004 | Nadel et al. | 435/6 |
| 2006/0222227 A1* | 10/2006 | Seul et al. | 382/128 |
| 2008/0219891 A1* | 9/2008 | McDevitt et al. | B01L 2200/0668 |
| 2009/0137053 A1 | 5/2009 | Kishii et al. | |
| 2009/0279787 A1* | 11/2009 | Kishii et al. | 382/195 |
| 2009/0308886 A1* | 12/2009 | Chang et al. | 222/1 |

FOREIGN PATENT DOCUMENTS

| | | |
|---|---|---|
| JP | 2008-505321 | 11/2009 |
| WO | 2005026729 A2 | 3/2005 |

OTHER PUBLICATIONS

"A continuous size-dependent particle separator using a negative dielectrophoretic virtual pillar array", Chang Sunghwan et al., Lab on a Chip, vol. 8, No. 11, 2008, pp. 1930-1936, XP002627289.

"A three-dimensional (3D) particle focusing channel using the positive dielectrophoresis (pDEP) guided by a dielectric structure between two planar electrodes", Chu Hyunjung et al: Lab on a Chip, vol. 9, No. 5, 2009, pp. 686-691, XP002627290, ISSN: 1473-0197.

"Development of an automated DNA purification module using a micro-fabricated pillar chip", Analyst, Royal Society of Chemistry, GB, vol. 133, No. 2, Feb. 1, 2008, pp. 248-255, XP009135720, ISSN: 0003-2654, DOI: DOI:10.1039/B713332D [retrieved on Dec. 6, 2007].

EP Search Report corresponding to 10014698.4 dated Mar. 24, 2011; 7 pages.

* cited by examiner

CELL FOR TESTING MICROBEADS AND METHOD OF ANALYZING MICROBEADS

CROSS REFERENCES TO RELATED APPLICATIONS

The present application claims priority to Japanese Priority Patent Applications JP 2010-154877 filed in the Japan Patent Office on Jul. 7, 2010, and JP 2010-284726 filed in the Japan Patent Office on Dec. 16, 2009, the entire content of which is hereby incorporated by reference.

BACKGROUND

The present application relates to a test cell. More particularly, the application relates to a test cell for use in analysis of microbeads.

In biochemical analysis of nucleic acids or proteins or the like, particulate supports called "microbeads" have been used. For instance, in nucleic acid analysis, microbeads on the surfaces of which a probe nucleic acid chain having a base sequence complementary to a target nucleic acid chain is fixed as a solid phase have been used to separate the target nucleic acid chain on the basis of its interaction with the probe nucleic acid chain. Similarly, in protein analysis, microbeads on the surfaces of which an antibody relevant to a target protein is fixed as a solid phase have been used to separate the target protein.

The target nucleic acid chain or the target protein separated through trapping on the surfaces of the microbeads can be optically detected by preliminarily labeling it with a fluorescent substance. In addition, by measuring the fluorescence intensity of the bead surfaces, it is also possible to determine the target substance thus separated. Where the target substance is a nucleic acid chain, an intercalator capable of emitting fluorescent light by being taken in between hybrid chains formed by an interaction between the target nucleic acid chain and the probe nucleic acid chain has been used to optically detect the target nucleic acid chain separated.

Now, an example of optical detection method for microbeads will be described. First, a dispersion in which microbeads are dispersed is placed on a measuring substrate, and a cover glass is disposed on that surface of the measuring substrate on which the dispersion is placed, to form a cell for measurement. Light is cast from a light source provided over the cell, and a transmission image or fluorescent image of the microbeads is picked up by an imaging device such as CCD or CMOS arranged over the cell.

For more information, refer to Japanese Patent Laid-open No. 2009-270946, JP-T-2005-504275 and JP-T-2008-505321.

SUMMARY

Microbeads often are minute things having a diameter and a thickness on the micrometer order (several micrometers to several hundreds of micrometers). When the concentration of microbeads in a dispersion is raised for enhancing detection efficiency, therefore, there may arise a problem that the microbeads overlap each other over the measuring substrate and it is very difficult to achieve normal imaging of the overlapping microbeads.

Thus, there is a need for a test cell in which microbeads are prevented from overlapping each other and analysis with high accuracy can be achieved.

In order to meet the above need, according to an embodiment, there is provided a cell for testing microbeads, used for testing microbeads each formed in a cylindrical shape having an upper surface and a lower surface opposite to and substantially parallel to each other and a side surface continuous with the upper and lower surfaces, at least one of the upper surface and the lower surface being provided with an identification pattern, wherein the cell includes a support substrate and a cover disposed opposite to the support substrate. The space between the support substrate and the cover forms a containing space in which to dispose the microbeads, and the distance between the support substrate and the cover is set to be greater than the thickness of the microbeads and smaller than twice the thickness of the microbeads.

Either one or both of the support substrate and the cover may be provided with a pillar. Preferably, the height of the pillar is greater than the thickness of the microbeads and smaller than twice the thickness of the microbeads. Further, preferably, the pillar is provided with at least one cutout smaller than at least one of the diameter of the upper surface of the microbead and the diameter of the lower surface of the microbead.

The pillar may be so formed as to surround the containing space, and the cover may be formed with a through-hole through which the containing space is connected to the external space. In this case, preferably, an absorbing member is disposed to face the cutout. Further, preferably, the support substrate is formed with a mount part where that portion of the support substrate which faces the containing space is projected to be higher than the other portion, and the absorbing member is disposed at an edge part lower than the mount part of the support substrate.

In addition, the cell may be provided with a supply port and a discharge port through which the containing space and the external space are connected to each other. In this case, the pillar is located between the supply port and the discharge port, whereby the containing space is partitioned into a supply space on the supply port side and a discharge space on the discharge port side. Preferably, the supply space is provided with a swollen part swelled toward the discharge port.

A reflecting mirror may be disposed at least at a part of that portion of the support substrate which faces the containing space.

In addition, according to another embodiment, there is provided a method of analyzing microbeads each formed in a cylindrical shape having an upper surface and a lower surface opposite to and substantially parallel to each other and a side surface continuous with the upper and lower surfaces, at least one of the upper surface and the lower surface being provided with an identification pattern. The analyzing method (testing method) include: a containing step of disposing a support substrate and a cover opposite to each other with a distance therebetween greater than the thickness of the microbeads and smaller than twice the thickness of the microbeads, and disposing the microbeads in a containing space between the support substrate and the cover; and an imaging step of imaging the microbeads present in the containing space.

In the containing step, preferably, the containing space is connected to a supply unit and a discharge unit, a pressure difference is generated between the supply unit and the discharge unit, and a dispersion in which the microbeads are dispersed is sucked into the containing space. Besides, in the containing step, preferably, a vibrational force is transmitted to a flow channel between the supply unit and the discharge unit so as to agitate the dispersion.

According to the present application, microbeads are prevented from overlapping each other, imaging of each of the microbeads can be performed easily, and, therefore, a target substance can be analyzed with high accuracy.

Additional features and advantages are described herein, and will be apparent from the following Detailed Description and the figures.

DETAILED DESCRIPTION

Figure 1A:
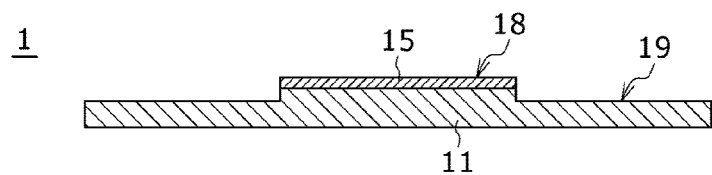
FIGS. 1A and 1B are sectional views illustrating a support substrate and a cover used in the present application.

Embodiments of the present application will be described below in detail with reference to the drawings.

Now, preferred modes for carrying out the present application will be described below referring to the drawings. Incidentally, the following are descriptions of a first embodiment and a second embodiment as representative modes for carrying out the application, which are not limitative of the scope of the application. The description below will be made in the following order.

Figure 1B:
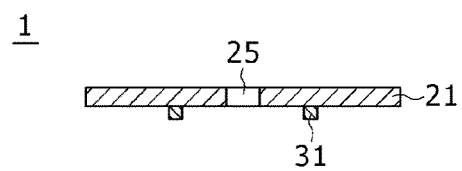

A. First Embodiment
 1. Test cell
  1a. Support substrate
  1b. Cover
  1c. Pillar
  1d. Assembled state
 2. Testing Method
  2a. Object to be tested (Microbeads)
  2b. Specific procedure of testing steps
B. Second Embodiment
 1. Test cell
  1a. Support substrate
  1b. Cover
  1c. Pillar
  1d. Assembled state 2. Testing Method
  2a. Object to be tested (Microbeads)
  2b. Specific procedure of testing steps A. First Embodiment 1. Test Cell Symbol 1 in FIGS. 1A and 1B denotes an example of the cell for testing microbeads according to an embodiment, and it will be hereinafter referred to as "test cell." The test cell 1 includes a support substrate 11, a cover 21, and a pillar 31. The support substrate 11 and the cover 21 are separable. FIG. 1A is a sectional view of the support substrate 11 in the separated state, and FIG. 1B is a sectional view of the cover 21 in the separated state.

1a. Support Substrate

The plan-view shape of the support substrate 11 is not particularly limited but may be a rectangle, a square, a circle, an ellipse or the like; here, the support substrate 11 is a rectangular plate. Of the support substrate 11, a central portion (here, a central portion in the longitudinal direction) is projected to be higher than an edge part 19, to be a mount part 18 on which to mount the cover 21 described later.

A reflecting mirror 15 is disposed at the mount part 18. The reflecting mirror 15 is not specifically limited; for example, it may be composed of a reflective metallic film formed from a reflective metallic material such as aluminum, silver, stainless steel, etc. by plating, vapor deposition, sputtering or the like. The place where to dispose the reflecting mirror 15 is not particularly limited. When the support substrate 11 is transparent, the reflecting mirror 15 may be embedded in the mount part 18 or may be disposed on the back surface, on the side opposite to the surface (face-side surface) on which to mount the cover 21, of the mount part 18. Preferably, however, the reflecting mirror 15 is disposed on the face-side surface of the mount part 18.

In the case of disposing the reflecting mirror 15 on the face-side surface of the mount part 18, for enhancing wettability of the reflecting mirror 15 for wetting with a dispersion which will be described later, a transparent resin film high in affinity for the dispersion (for instance, high in hydrophilicity) may be formed on the surface of the reflecting mirror 15. In this case, the material and thickness of the resin film are preferably so designed as to prevent generation of interference fringe or the like due to reflected light from the surface of the resin film and the surface of the reflecting mirror 15. The reflecting mirror 15 may be so disposed as to cover the mount part 18 entirely, or may be disposed only in an imaging region where microbeads are imaged as described later.

1b. Cover 21

The cover 21 is a transparent plate, and is provided in its central portion with a through-hole 25 penetrating the cover 21 from the face-side surface to the back surface, as a supply port. The plan-view shape of the cover 21 is not specifically restricted, but may be a rectangular shape (inclusive of squares and rectangles), a circular shape (inclusive of true circles and ellipses) or the like; here, the plan-view shape is a square.

1c. Pillar

Figure 3:
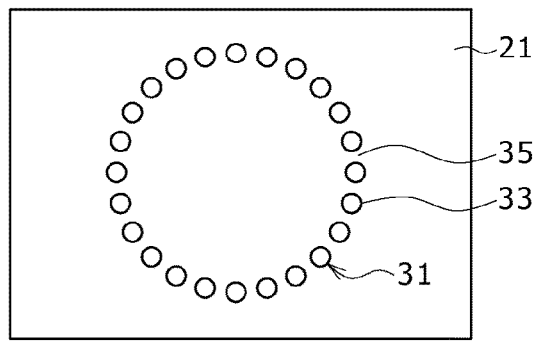
FIG. 3 is a plan view illustrating a first example of a pillar in the application.
Figure 4:
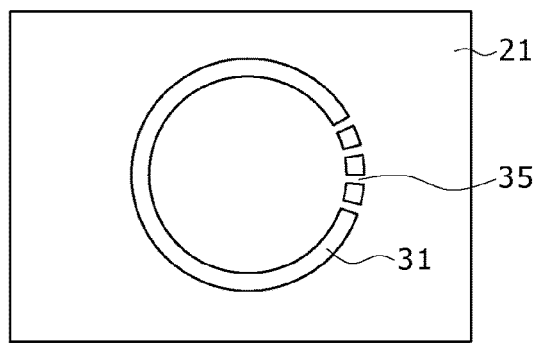
FIG. 4 is a plan view illustrating a second example of the pillar in the application.
Figure 5:
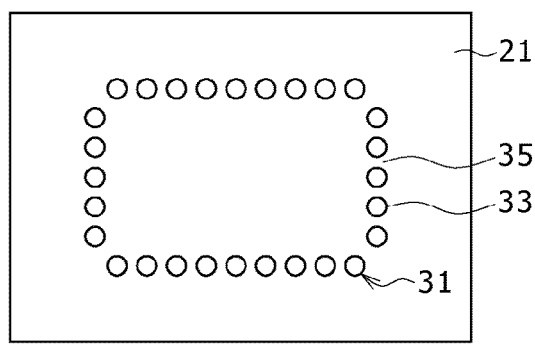
FIG. 5 is a plan view illustrating a third example of the pillar in the application.
Figure 6:
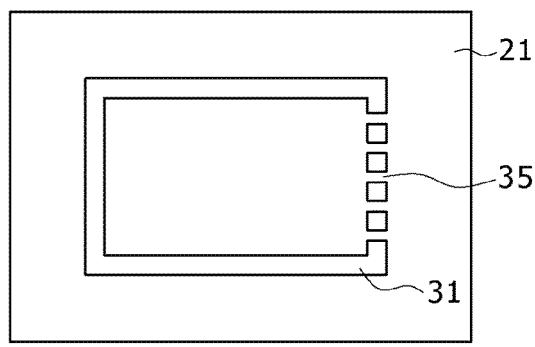
FIG. 6 is a plan view illustrating a fourth example of the pillar in the application.

The pillar 31 projecting from a surface is fixed to either one or both of the support substrate 11 and the cover 21. Here, the pillar 31 is projected from the surface of the cover 21. The plan-view shape of the pillar 31 is not particularly limited; as shown in FIGS. 3 to 6, however, the pillar 31 is ring-like in plan-view shape, and is provided with one or a plurality of cutouts 35. The ring-like shape of the pillar 31 may be a circular shape (inclusive of true circles and ellipses) as shown in FIGS. 3 and 4, or may be a rectangular shape (inclusive of squares and rectangles) as shown in FIGS. 5 and 6; further, it may be a triangle or a polygon having five or more vertexes.

In addition, the pillar 31 may be formed by forming one or more cutouts 35 in a ring-shaped pillar 31 as shown in FIGS. 4 and 6, or may be formed by arranging a plurality of pillar members 33 as shown in FIGS. 3 and 5. In the case where the pillar 31 is formed by arranging a plurality of pillar members 33, the pillar members 33 are disposed at intervals so that the gaps between the pillar members 33 constitute the cutouts 35. In this case, some of the pillar members 33 may be fixed to the support substrate 11 whereas the other pillar members 33 may be fixed to the cover 21, in such a manner that the overall shape of the pillars 31 in the assembled state (described later) will be a ring-like shape.

Materials of the support substrate 11, the cover 21 and the pillar 31 are not specifically restricted. Examples of the materials for forming these components include glass, quartz, and various plastics (PP (polypropylene), PC (polycarbonate), COP (cyclo-olefin polymer), PDMS (polydimethylsiloxane), etc.). The materials are preferably those which are transparent to a laser beam radiated from a detecting portion, which show little autofluorescence, and which produce little optical errors because of small wavelength dispersion.

Particularly preferable materials include glass, acrylic resins, polycarbonate resins, and COC (cycloolefin copolymer resins), which are inexpensive and, hence, make it possible to lower the manufacturing cost of the test cell 1 as a whole and to render the test cell 1 disposable.

At least those portions of the support substrate 11, the cover 21 and the pillar 31 which are exposed to the surface are each preferably formed from a material high in wettability with the dispersion (described later). Forming (shaping) of the mount part 18, the through-hole 25, the pillar 31 and the like can be carried out by wet etching or dry etching of a glass substrate or by nano-imprinting, injection molding or mechanical working of a plastic substrate.

1d. Assembled State

The orientation of the cover 21 at the time of mounting the cover 21 on the support substrate 11 is predetermined. Thus, the cover 21 is disposed on the mount part 18 of the support substrate 11 in the predetermined orientation, resulting in an assembled state. The plan-view shape of the pillar 31 is such that the inner circumference of the ring-like shape thereof is equal to or smaller than the outer circumferences of the plan-view shapes of the cover 21 and the mount part 18. In the assembled condition, the pillar 31 is clamped between the mount part 18 and the cover 21, and the space on the inside of the ring-like shape of the pillar 31 is closed with the cover 21 and the mount part 18, to be a containing space 39 in which to contain the microbeads described later.

Besides, the inner circumference of the ring-like shape of the pillar 31 is greater than the through-hole 25 in the cover 21, and the through-hole 25 is located in a central portion of the cover 21. Therefore, in the assembled state, the pillar 31 makes contact with the edge part, on the outside relative to the through-hole 25, of the cover 21, and the through-hole 25 is located on the upper side of the containing space 39. In other words, in the assembled condition, the containing space 39 is connected to the external space (exterior) via the through-hole 25 and the cutouts 35 in the pillar 31.

Figure 2A:
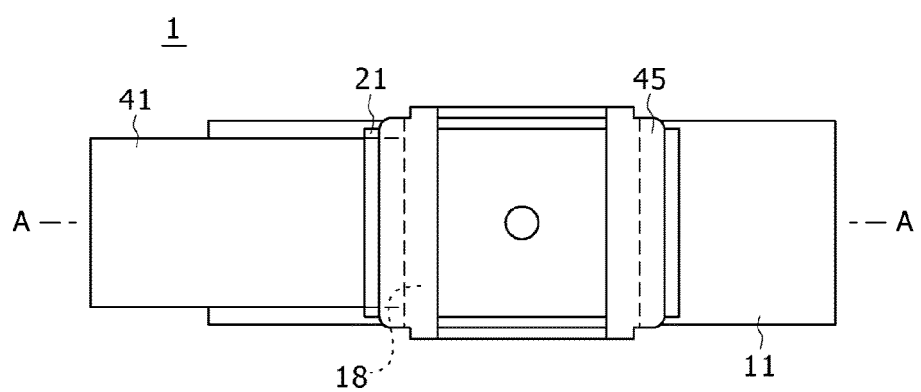
FIGS. 2A and 2B are a plan view and a sectional view illustrating an assembled state of a test cell according to a first embodiment of the application.
Figure 2B:
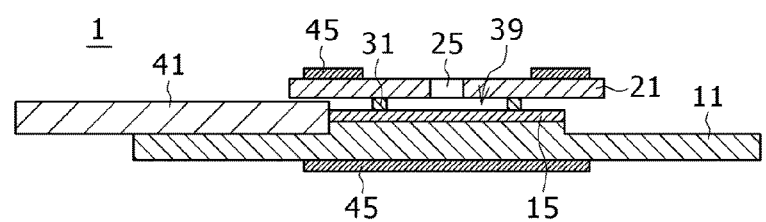

FIG. 2A is a plan view of the assembled state, and FIG. 2B is a sectional view taken along line A-A of FIG. 2A. In the assembled state, if necessary, the cover 21 may be fixed to the support substrate 11 by a fixing member 45 or the like, for the purpose of preventing misalignment. The plan-view shape of the support substrate 11 is set to be greater than that of the cover 21, in such a manner that a part or the whole part of the edge part 19 on the outer side relative to the mount part 18 protrudes to the outside beyond the edge of the cover 21.

Preferably, a sheet-shaped absorbing member 41 is disposed on the edge part 19 exposed from the cover 21. That area of the edge part 19 in which to arrange the absorbing member 41 is predetermined. In that area, the edge part 19 is exposed not only from the cover 21 but also from other members such as the fixing member 45, so that the arrangement of the absorbing member 41 is not hampered. Incidentally, the area in which to arrange the absorbing member 41 is not specifically restricted. The absorbing member 41 may be clamped in a sandwiched manner by providing an edge of the lower surface of the cover 21 with a step or chamfer.

In the case where a liquid phase is absorbed by capillarity as described later, the absorbing member 41 is preferably set as close as possible to the step at the boundary between the mount part 18 and the edge part 19, or set in contact with the step. In the case where the boundary between the mount part 18 and the edge part 19 where the absorbing member 41 is arranged is located on the inner side relative to the edge of the cover 21, if the thickness of the absorbing member 41 is set to be smaller than the height from the surface of the edge part 19 to the surface of the cover 21, the absorbing member 41 enters into the gap between the cover 21 and the edge part 19, to make contact with the step present at the boundary portion.

Where the above-mentioned boundary and the edge of the cover 21 are flush with each other, the absorbing member 41 makes contact with the step even if the thickness of the absorbing member 41 is greater than the height from the surface of the edge part 19 to the surface of the cover 21. However, it is more preferable for the absorbing member 41 to be put in the gap between the cover 21 and the edge part 19, since the absorbing member 41 is thereby disposed stably. In both cases, preferably, the thickness of the absorbing member 41 is set to be greater than the height from the surface of the edge part 19 to the surface of the mount part 18, and the absorbing member 41 is made to face the gap between the mount part 18 and the cover 21.

2. Testing Method

2a. Object to be Tested (Microbeads)

Figure 7:
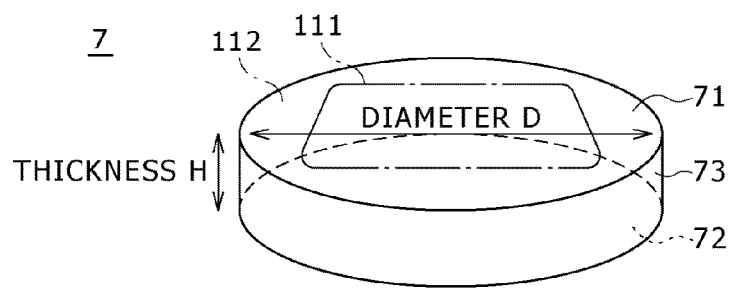
FIG. 7 is a perspective view illustrating an example of microbead.

As an object to be tested by the test cell 1 according to an embodiment, there is used a microbead which is provided with an identification pattern (ID pattern) on a surface thereof and on which a substance having affinity for an object substance to be detected is fixed as a solid phase. FIG. 7 illustrates an example of the microbead.

The microbead 7 is formed in a columnar shape which has an upper surface 71 and a lower surface 72 opposite to and substantially parallel to each other and a side surface 73 continuous with the upper and lower surfaces 71, 72. Here, description will be made referring to an exemplary case where the upper surface 71 and the lower surface 72 are circular in top plan view and the microbead 7 as a whole is cylindrical in shape. However, the microbeads to be used in the present application may be in the shape of a triangular prism, a tetragonal prism or other polygonal prism. However, since a transmission image inclusive of the ID pattern is to be obtained by a method which will be described later, the microbeads 7 should be formed in a columnar shape having the upper surface 71 and the lower surface 72 opposite to and substantially parallel to each other.

The thickness H and the diameter D of the upper surface 71 (or the lower surface 72) of the microbead 7 may be set as required. It is preferable, however, to set the thickness H to be smaller than the diameter D so that the microbead 7 as a whole is disk-like in shape.

At least one (in FIG. 7, the upper surface 71) of the upper surface 71 and the lower surface 72 of the microbead 7 is provided with a code region 111 in which a pattern for image identification of each individual bead is formed. Of the upper surface 71, the other region than the code region 111 is a non-code region 112 where the ID pattern is not formed. The code region 111 may be provided on the lower surface 72, or may be provided on both the upper surface 71 and the lower surface 72.

The ID pattern is not specifically restricted. For instance, a through-hole or through-holes penetrating the microbead 7 from the upper surface 71 to the lower surface 72 are formed in the code region 111, and the through-hole or through-holes constitute the ID pattern. The microbeads 7 can be identified (discriminated) by the differences in the number of the through-hole(s) formed and/or the site(s) where the through-hole(s) are formed.

The number of the through-hole(s) formed in the code region 111 may be any number in the range from 0 to 25, and the through-hole(s) are formed at arbitrary position(s) selected from 25 positions. Thus, in the microbeads 7, different patterns can be formed in the code regions 111 of the individual microbeads 7 by arbitrarily setting the number of the through-hole(s) formed and/or the position(s) where the through-hole(s) are formed. With these patterns detected by an image identification portion, it is possible to identify a maximum of 225 kinds of microbeads 7.

Incidentally, the ID pattern described above is merely an example. The ID patterns formed on the microbeads 7 to be used in the present application are not specifically restricted in shape, size or the like insofar as their shapes can be identified (discriminated) by known image identification means.

On the surface of the microbead 7, a substance having affinity for the object substance to be detected is fixed as a solid phase. Hereinafter, the object substance to be detected will be referred to as "target substance," and the substance having affinity for the object substance to be detected will be referred to as "probe substance."

The probe substance is fixed on the surface of the microbead 7 as a solid phase. The probe substance is a nucleic acid having a predetermined base sequence, a protein or peptide having a predetermined amino acid sequence, or a sugar chain or the like compound, according to the target substance. The probe substance is fixed as a solid phase on at least the upper surface 71 inclusive of both the code region 111 and the non-code region 112 and the side surface 73, and, in addition, may be fixed as a solid phase on the lower surface 72 also. Incidentally, in the case where the ID pattern is formed also on the lower surface 72, the probe substance may be fixed as a solid phase on both a code region and a non-code region of the lower surface 72 also.

Where the target substance is a nucleic acid, the probe substance is a nucleic acid chain having a base sequence complementary to the target nucleic acid chain. This ensures that the target nucleic acid chain in a sample can be separated by trapping it on the microbeads 7 through formation of hybridization (double strand) with the probe substance. Incidentally, the number (length) of the bases of the probe substance in this case is arbitrary. Specifically, the number of bases is not particularly limited insofar as the probe substance has a base sequence complementary to at least a part of the base sequence of the target nucleic acid chain and a double strand can be formed under predetermined hybridization reaction conditions. Ordinarily, the probe substance has several to several tens of bases, and a preferable number of bases is about 10 to 30.

Where the target substance is a protein, the probe substance is a peptide (e.g., a partial amino acid sequence of a ligand protein) or an antibody or the like capable of interaction with the target protein (e.g., receptor protein). This ensures that the target protein in a sample can be separated by trapping it on the microbead 7 through the interaction with the probe substance.

The microbead 7 with the target substance trapped thereon comes to emit fluorescent light, based on the interaction between the probe substance and the target substance. The fluorescent light may be generated from a fluorescent substance used to label the target substance or from an intercalator taken in between the probe substance and the target substance. In the microbead analyzing method according to an embodiment, simultaneously with the detection of such fluorescent light, the ID patterns formed on the individual microbeads 7 are identified by an image identification portion, whereby a plurality of kinds of target substances are analyzed simultaneously.

2b. Specific Procedure of Testing Steps (i) Procedure of Reaction

First, the microbeads 7 are mixed with a sample containing a target substance, to bring a probe substance fixed as a solid phase on the microbead surfaces into interaction with the target substance, thereby trapping the target substance on the microbead surfaces.

The mixing of the microbeads 7 with the sample is carried out after labeling the target substance with a fluorescent substance, or carried out in the presence of an intercalator capable of emitting fluorescent light by being taken into a complex formed through interaction between the target substance and the probe substance.

(ii) Holding Procedure

Next, the microbeads 7 are recovered, optionally followed by washing (cleaning) so as to remove substances (foreign matter) other than the target substance adsorbed on the microbeads 7, and the microbeads 7 are dispersed in a liquid phase, to prepare a dispersion. Incidentally, the liquid phase used here is preferably composed of a liquid having a refractive index equal to that of the microbeads 7; however, a buffer or pure water used in the above-mentioned reaction procedure may be used as the liquid phase here. More preferably, the liquid phase is composed of the buffer used in the above-mentioned reaction procedure or a buffer higher than the above-mentioned buffer in base concentration. When such a buffer is used, the target substance trapped on the microbeads 7 is less liable to be denatured or dissociated.

The through-hole 25 in the cover 21 is greater than the diameter(s) D of the upper surface 71 and the lower surface 72 of the microbeads 7. Moreover, the cover 21 is formed from a material high in wettability with the liquid phase of the dispersion. Therefore, when the dispersion is injected into the through-hole 25 in the test cell 1 in the assembled state, the microbeads 7 are injected into the containing space 39 via the through-hole 25, together with the liquid phase.

When the containing space 39 is sealed up, it is difficult to inject the dispersion into the containing space 39, and a bubble (air) may be left in the containing space 39. In addition, that portion of the dispersion which cannot be fed into the containing space 39 may swell up in a convex lens-like shape over the through-hole 25. In the present application, the pillar 31 is provided with the cutouts 35 as shown in FIGS. 3 to 6, so that air is pushed out through the cutouts 35. Accordingly, the dispersion is easily injected into the containing space 39, the containing space 39 is filled up with the dispersion, and the dispersion would not be left over the through-hole 25.

Orientation of the microbeads 7 on the test cell 1 is achieved by a method in which the thickness H of the microbead 7 is set to be smaller than the diameter D of the upper surface 71 (or the lower surface 72) so that the microbead 7 as a whole is disk-like in shape. Specifically, the microbeads 7 are each so oriented that the upper surface 71 and the lower surface 72 thereof are disposed in parallel to the surfaces of the cover 21 and the mount part 18.

The height of the pillar 31 (the pillar members 33) is set to be greater than the thickness D of the microbeads 7 and smaller than twice the thickness D. In other words, in the containing space 39, the height from the support substrate 11 (the mount part 18) to the cover 21 is greater than the thickness D of the microbeads 7 and smaller than twice the thickness D, which ensures that the microbeads 7 are disposed in the containing space 39 without overlapping each other.

The cutout 35 in the pillar 31 (the gap between the pillar members 33) is set to be smaller than the diameter D of at least one of the upper surface 71 and the lower surface 72 of the microbead 7. This ensures that, although the liquid phase of the dispersion is pushed out through the cutouts 35 together with air, the microbeads 7 do not pass through the cutouts 35 but are left in the containing space 39.

Incidentally, in the case where microbeads differing in size and/or shape are to be tested on the same test cell 1, it is preferable that the through-hole 25 in the cover 21 is set greater than the diameter D of the largest microbeads and that the cutouts 35 are each smaller than the diameter D of the smallest microbeads. Besides, it is preferable that the height of the pillar 31 is set greater than the thickness H of the largest microbeads and smaller than twice the thickness H of the smallest microbeads.

In addition, of the support substrate 11 and the cover 21, one on the side on which the pillar 31 is fixed may be replaced, whereby it is possible to assemble a test cell for a target to be tested that is different in size and/or shape from the target to be tested relevant to the original test cell.

At the time of injecting the dispersion, the above-mentioned absorbing member 41 is preferably so disposed that the absorbing member 41 faces the gap between the mount part 18 and the cover 21 and comes into contact with or proximity to the step at the boundary between the mount part 18 and the edge part 19. The absorbing member 41 is obtained by forming such a material as paper, nonwoven fabric, sponge, etc. into a sheet-like shape, and has a capillary structure.

In general, the microbeads 7 are small, with a diameter D of about 40 μm and a height H of about 10 μm. Since the distance between the mount part 18 and the cover 21 is less than twice the height H, or less than about 20 μm, the gap is so narrow that capillary attraction is applied to a liquid phase. Accordingly, the capillarity causes the liquid phase of the dispersion to pass through the cutouts 35 and through the gap between the mount part 18 and the cover 21, thereby moving to the side of the absorbing member 41, to be absorbed into the absorbing member 41.

Since the gap between the cover 21 and the mount part 18 is narrow, the internal volume of the containing space 39 is no more than about several microliters. However, since a large amount of the dispersion can be injected owing to the absorbing member 41 and the microbeads 7 are prevented from flowing away via the cutouts 35, the amount of the microbeads 7 disposed in the containing space 39 is large. Moreover, the enhanced injection efficiency lowers the possibility of a bubble or bubbles being left in the containing space 39. In order to enhance the efficiency of absorption into the absorbing member 41, the arrangement site of the absorbing member 41 is preferably so set that the portion provided with the cutouts 35, of the pillar 31, faces the absorbing member 41.

As above-mentioned, the microbeads 7 are held while being so oriented that either of the two surfaces (the upper surface 71 and the lower surface 72) opposite to and substantially parallel to each other makes contact with the surface of the mount part 18. With the microbeads 7 held in such an orientation, the ID pattern formed in the code region(s) on the upper surface 71 and/or the lower surface 72 can be imaged by an image pick-up portion (not shown) disposed to face the surface, on the side of the cover 21, of the test cell 1.

(iii) Testing Procedure
(a) Detection of ID Pattern

A test cell 1 with the microbeads 7 contained therein in the state of being suspended in a liquid phase is used. Where the liquid phase may be lost through drying, the liquid phase is additionally dropped, as required, to ensure that the microbeads 7 are always contained in the liquid phase. A light source is disposed over the surface, on the side of the cover 21, of the test cell 1, and the microbeads 7 in the containing space 39 are irradiated with the light from the light source through the cover 21. An image pick-up portion (not shown) is arranged at a position where the light transmitted through the cover 21 is incident, and a transmission image and a fluorescent image of the microbeads 7 are picked up by the image pick-up portion. Since overlapping of the microbeads 7 is prevented in the test cell 1 in the present embodiment, the microbeads 7 present in an imaging region can all be imaged normally.

In this instance, if a bubble (air) remains in the containing space 39, an interference fringe would be generated by interference of light due to the air layer. Besides, when the dispersion is swollen up in a convex lens-like shape over the through-hole 25, light would be condensed by the dispersion liquid. In both cases, the image picked up would be obscure. Where the pillar 31 is provided with the cutouts 35 as above-described, both of remaining of air in the containing space 39 and remaining of the dispersion over the through-hole 25 are prevented, and, therefore, it is possible to obtain a clear transmission image and a clear fluorescent image.

Since the microbead 7 is so oriented that either the upper surface 71 or the lower surface 72 makes contact with the surface of the mount part 18, it can be ensured that the transmission image picked up by the image pick-up portion includes the ID pattern without fail. Where the reflecting mirror 15 is disposed on the mount part 18, the light traveling from the microbead 7 toward the side of the mount part 18 is reflected toward the image pick-up portion side, so that the quantity of detection light incident on the image pick-up portion is increased. Consequently, the transmission image and the fluorescent image become clear, and the S/N is enhanced, whereby a signal output to an analyzing portion can be enhanced.

Figure 9A:
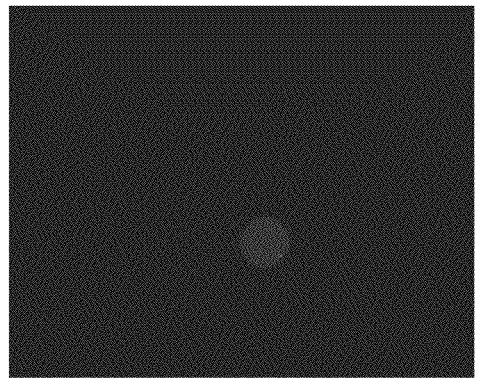
FIGS. 9A and 9B are images picked up in the absence of a reflecting mirror.
Figure 9B:
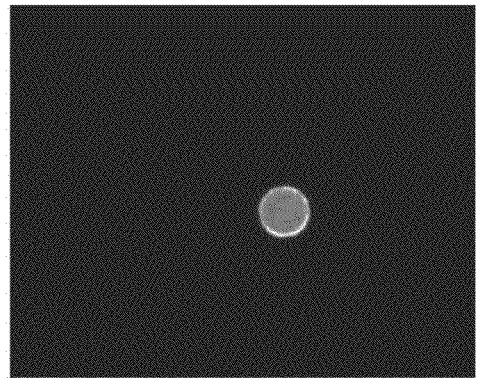
Figure 9C:
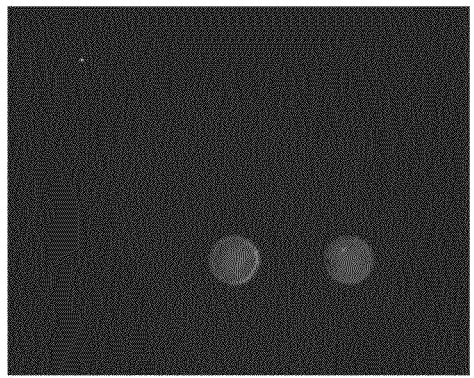
FIGS. 9C and 9D are images picked up in the presence of a reflecting mirror.
Figure 9D:
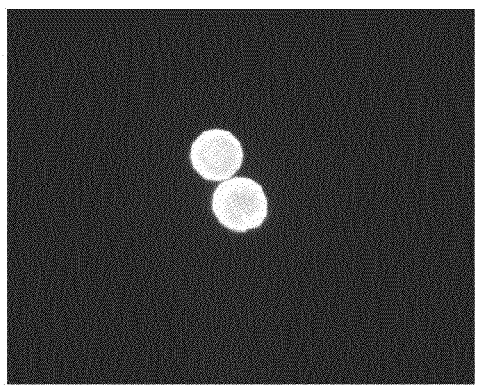

FIGS. 9A and 9B show fluorescent images picked up in the case where a glass support substrate 11 was used without providing a reflecting mirror, and FIGS. 9C and 9D show fluorescent images picked up in the presence of an aluminum reflecting mirror 15. FIGS. 9A and 9C correspond to the case where a target substance non-complementary to the probe substance on the microbeads 7 is made to act (mis-match), while FIGS. 9B and 9D correspond to the case where a target substance complementary to the probe substance on the microbeads 7 is made to act (full-match). It is seen that the use of the reflecting mirror 15 makes conspicuous the difference between mis-match and full-match, thereby enhancing the S/N.

(b) Detection of Fluorescent Light

The fluorescent image picked up by the image pick-up portion is outputted to a fluorescent light detection portion. The fluorescent light detection portion detects fluorescent light coming from a predetermined region of the fluorescent image, converts the intensity of the fluorescent light into an electrical signal, and outputs the signal to the analyzing portion.

On the other hand, the transmission image picked up by the image pick-up portion is outputted to an image identification portion. The image identification portion detects the ID pattern from the transmission image, converts the ID pattern into an electrical signal, and outputs the signal to the analyzing portion. Detection of the ID pattern can be carried out using a general-purpose image analysis program or an appropriately improved derivative thereof.

As above-described, the test cell 1 in the present application is so configured that the microbeads 7 would not overlap each other. Therefore, the microbeads 7 present in the imaging region can all be imaged, and the target substance can be analyzed with high accuracy.

Figure 8:
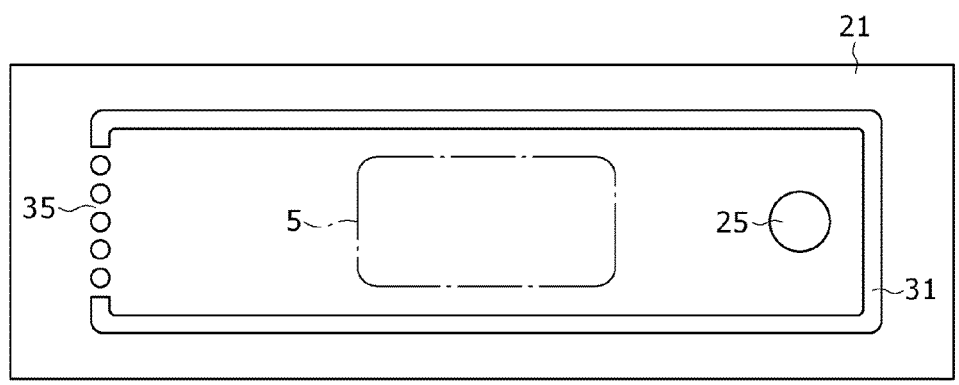
FIG. 8 is a plan view illustrating another example of the positional relationship between the pillar and a through-hole in the application.

Incidentally, the positional relationship between the region (imaging region) relevant to imaging of the microbeads 7 and the members (the pillar 31, the through-hole 25, etc.) of the test cell 1 is not particularly restricted. For instance, as shown in FIG. 8, the through-hole 25 may be provided outside the imaging region 5. In this case, even if the dispersion is left over the through-hole 25, it does not influence the imaging. In the case where the through-hole 25 is provided outside the imaging region 5, arrangement of the imaging region 5 between the through-hole 25 and the cutouts 35 ensures that, when the dispersion is injected, bubbles in the imaging region 5 are washed away and discharged via the cutouts 35 together with the surplus liquid phase.

In the case where the imaging region 5 is part of the mount part 18, it is unnecessary for the reflecting mirror 15 to be provided on the whole part of the mount part 18, and it suffices to provide the reflecting mirror 15 at least on that part of the mount part 18 which faces the imaging region 5. The mount part 18 may be flush with the edge part 19. In the case of providing the reflecting mirror 15, however, the thickness of the mount part 18 is increased by the thickness of the reflecting mirror 15, and, therefore, setting the mount part 18 to be thicker than the edge part 19 makes it easier to dispose the reflecting mirror 15.

While the pillar 31 surrounding the containing space 39 is provided with the cutouts 35 in the embodiment described above, the present application is not limited to this configuration. A test cell according to a second embodiment of the application and a testing method based on the use of the test cell will be described below.

B. Second Embodiment

1. Test Cell

Figure 10:
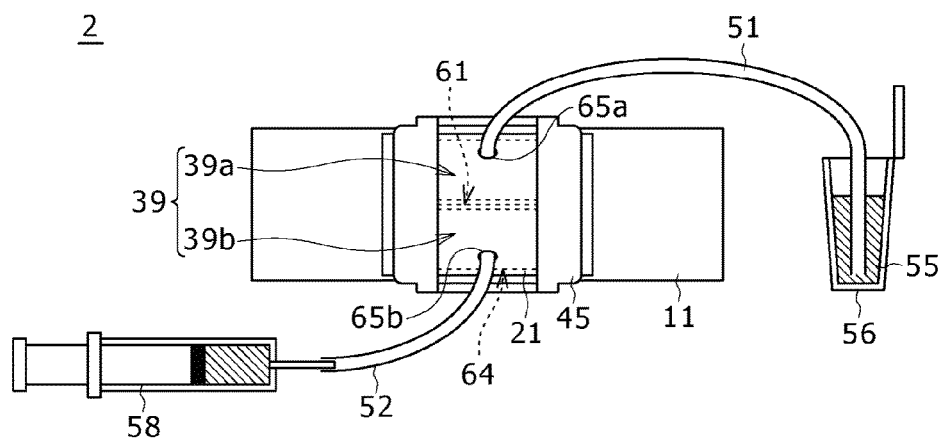
FIG. 10 is a schematic plan view of a test cell according to a second embodiment of the application.

Symbol 2 in FIG. 10 denotes a cell for testing microbeads according to a second embodiment. In the drawing, the members having the same structures as in the test cell 1 of the first embodiment above are denoted by the same symbols as used above.

1a. Support Substrate

A support substrate 11 is not specifically restricted. A support substrate which is the same as that shown in FIG. 1A in structure, shape, and material can be used. In the second embodiment, however, it is unnecessary that a part of the support substrate 11 should be made to be a mount part 18 higher than an edge part 19.

In the second embodiment, also, the support substrate 11 may be provided with a reflecting mirror 15. The site where to dispose the reflecting mirror 15 is not particularly restricted, but the reflecting mirror 15 is preferably disposed at least in a region (imaging region) where the microbeads 7 collect.

1b. Cover

A cover 21, also, is not specifically restricted. A cover which is the same as that shown in FIG. 1B in structure, shape, and material can be used. In the second embodiment, however, in the case of forming a through-hole or through-holes in the cover 21, the number of the through-hole(s) is preferably two or more. In this case, at least one through-hole can be provided as a supply port 65a for the microbeads 7, and at least one other through-hole can be provided as a discharge port 65b for the liquid phase.

1c. Pillar

A pillar, also, is not particularly limited. Pillars which are the same as those shown in FIGS. 1 to 6 and 8 in structure, shape, material, production method, and layout can be used. In the second embodiment, however, a pillar 61 having cutouts is formed to cross a containing space 39 so that the containing space 39 is partitioned by the pillar 61 into a supply space 39a connected to the supply port 65a and a discharge space 39b connected to the discharge port 65b. Incidentally, a ring-shaped pillar 64 for sealing the containing space 39 is preferably formed, in addition to the pillar 61. Hereinafter, for discrimination between the pillars, the pillar 64 surrounding the containing space 39 will be referred to as the sealing pillar, whereas the pillar 61 partitioning the containing space 39 will be referred to as the partition pillar.

The sites where to dispose the pillars 61 and 64 are not specifically restricted. It suffices that the pillars 61 and 64 are formed on either one or both of the support substrate 11 and the cover 21, in such a manner that the space (the containing space 39) inside the sealing pillar 64 is partitioned into two spaces by the partition pillar 61 when the test cell 2 is assembled, as will be described later.

The sealing pillar 64 and the partition pillar 61 may be the same or different in height. Preferably, however, the height of the higher one of the pillars 61 and 64 is set to be greater than the thickness H of the microbeads 7 and smaller than twice the thickness H.

1d. Assembled State

In the assembled condition, like in the first embodiment, the pillars 61 and 64 are clamped between the cover 21 and the support substrate 11, and the space inside the ring-like shape of the sealing pillar 64 is sealed by the support substrate 11 and the cover 21 and the sealing pillar 64. The cover 21 and the support substrate 11 are spaced from each other by an interval corresponding to the height of the pillars 61, 64. In other words, the cover 21 and the support substrate 11 are spaced from each other by a distance which is greater than the thickness H of the microbeads 7 and smaller than twice the thickness H. Thus, the space inside the ring-like shape of the sealing pillar 64 forms the containing space 39 in which the microbeads 7 can be contained.

The supply port 65a and the discharge port 65b mentioned above are spaced from each other, and are connected to the same containing space 39. Incidentally, the supply port 65a and the discharge port 65b are not limited to the through-holes formed in the cover 21. Either one or both of the supply port 65a and the discharge port 65b may be composed of through-holes formed in the sealing pillar 64 and/or the support substrate 11. Further, a configuration may be adopted in which piping or the like is led into the containing space 39, and the supply port 65a and/or the discharge port 65b is composed of one end of the piping.

The partition pillar 61 is located inside the ring-like shape of the sealing pillar 64 and between the supply port 65a and the discharge port 65b, so as to partition the containing space 39 into two spaces, namely, the supply space 39a on the side of the supply port 65a and the discharge space 39b on the side of the discharge port 65b.

Figure 11:
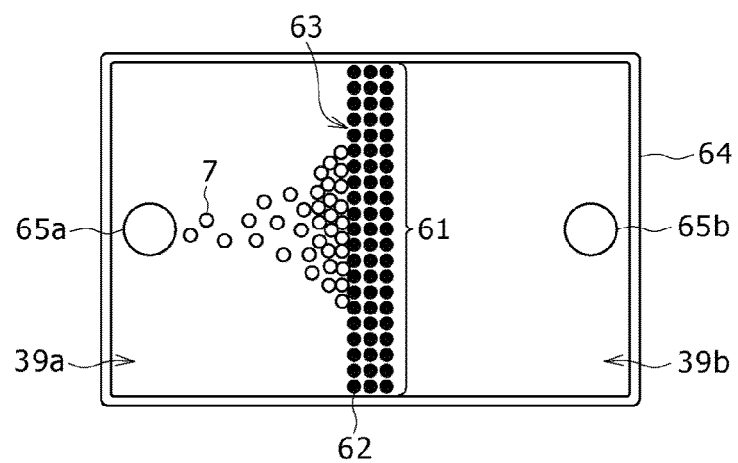
FIG. 11 is a schematic plan view (No. 1) for illustrating a partition pillar.
Figure 12:
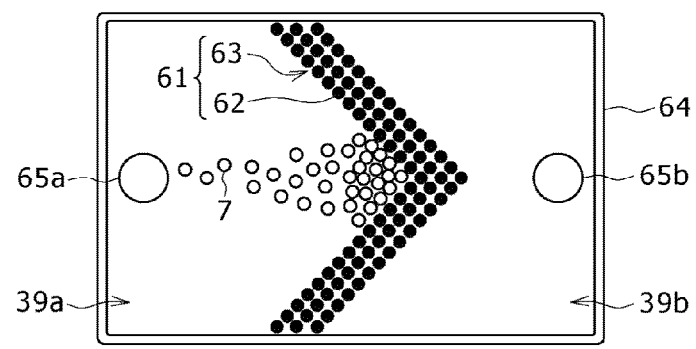
FIG. 12 is a schematic plan view (No. 2) for illustrating a partition pillar.
Figure 13:
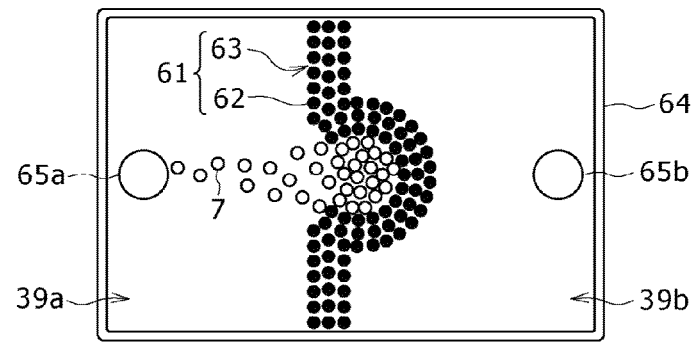
FIG. 13 is a schematic plan view (No. 3) for illustrating a partition pillar.

FIGS. 11 to 13 are plan views each schematically showing the positional relationship between the supply port 65a, the discharge port 65b and the partition pillar 61. The partition pillar 61 is composed of a row or rows of pillar members 62 formed across the ring-like shape of the sealing pillar 64. The pillar members 62 constituting one row are spaced from each other, and the spaces between the pillar members 62 constitute cutouts 63. Consequently, the supply space 39a and the discharge space 39b are connected to each other through the cutouts 63.

Incidentally, an elongated pillar member 62 may be provided with one or a plurality of cutouts 63, to form the partition pillar 61. In addition, the shape of the partition pillar 61 is not specifically restricted. The row of the pillar members 62 may be a straight line (FIG. 11), a hooked line (FIG. 12), a curved line (FIG. 13) or the like. Besides, the number of the row(s) of the pillar members 62 constituting the partition pillar 61 may be one or two or more.

2. Testing Method

2a. Object to be Tested

The object to be tested on the test cell 2 in the second embodiment is not particularly limited, and the same microbeads 7 as used in the test cell 1 in the first embodiment above can be used.

2b. Specific Procedure of Testing Steps (i) Procedure of Reaction

The procedure of reaction, also, is not specifically restricted. A target substance can be trapped on the microbeads 7 by the same procedure as in the case of the test cell 1 in the first embodiment above.

(ii) Holding Procedure

The supply port 65a and the discharge port 65b are connected respectively to a supply unit 56 and a discharge unit 58, either directly or through pipings 51, 52 such as silicone tubes or Teflon (registered trademark) tubes. The supply unit 56 has a vessel such as Eppendorf tube, and a dispersion 55 of the microbeads 7 is preliminarily contained in the vessel.

Either one or both of the supply unit 56 and the discharge unit 58 have a pressure control portion. The pressure control portion possessed by the discharge unit 58 is a pressure reducing portion such as a syringe and a suction pump. The pressure control portion on the side of the supply unit 56 is a pressurizing portion such as a syringe and a pressure pump.

The containing space 39 is partitioned by the partition pillar 61 into the supply space 39a and the discharge space 39b. Since the partition pillar 61 is formed with the cutouts 63, however, the supply space 39a and the discharge space 39b are connected to each other through the cutouts 63. When a pressure difference is formed between the supply unit 56 and the discharge unit 58 by pressurization in the supply unit 56 by the pressurizing portion and/or pressure reduction in the discharge unit 58 by the pressure reducing portion, the pressure difference causes the dispersion 55 to flow from the supply unit 56 toward the discharge unit 58, whereby the supply space 39a is supplied with the dispersion 55.

The distance between the pillar members 62 constituting the row in the partition pillar 61 and the distance from the pillar member 62 at a terminal end of the row to the sealing pillar 64 are smaller than the diameter D of the microbeads 7. In other words, the cutouts 63 in the pillars 61, 64 are smaller than the diameter D of the microbeads 7. Therefore, though the liquid phase of the dispersion 55 passes through the cutouts 63, the microbeads 7 do not pass through the cutouts 63 but remain in the supply space 39a, resulting in an increase in the density of the microbeads 7 in the supply space 39a.

Here, the term "the diameter D of the microbeads 7" means the diameter D of at least one of the upper surface 71 and the lower surface 72 of the microbead 7. In the case where the upper surface 71 and the lower surface 72 are different from each other in diameter, the microbeads 7 can be retained in the supply space 39a if the cutouts 63 are smaller than the diameter of the larger one of the upper and lower surfaces 71, 72.

In the test cell 2 in the second embodiment, also, the height of the containing space 39 is greater than the thickness H of the microbeads 7 and smaller than the twice of the thickness H. Therefore, even when the density of the microbeads 7 is enhanced as above-mentioned, the microbeads 7 would not overlap each other.

Although the pillar members 62 may be provided in only one row, it is preferable to provide the pillar members 62 in two or more rows. Where the pillar members 62 are provided in a plurality of rows, even when the pillar member 62 in one row is broken or lost, the other row or rows prevent the microbeads 7 from flowing out.

The shape of the row of the pillar member 62 is not particularly restricted. However, where the row of the pillar members 62 is designed to project toward the discharge port 65b so that the supply space 39a is swollen toward the discharge port 65b, as shown in FIGS. 12 and 13, the microbeads 7 collect concentratedly in the swollen part of the supply space 39a, resulting in an increase in the density thereof.

With a configuration in which the swollen part of the supply space 39a is provided between the supply port 65a and the discharge port 65b and in which the supply port 65a and the swollen part and the discharge port 65b are aligned on a straight line, the microbeads 7 can be caused to collect in the swollen part more efficiently. When such a swollen part is set to be an imaging region, imaging of the microbeads 7 can be carried out more efficiently.

After the microbeads 7 are contained in the supply space 39a and before imaging is conducted, the microbeads 7 may be washed (cleaned) by supplying a cleaning liquid into the supply space 39a. The cleaning liquid may be supplied from the same supply unit 56 as that relevant to the dispersion 55, or may be supplied from a supply unit different from the supply unit of the dispersion 55. Preferably, a gas mixing preventive portion such as an air trap is provided and gases such as air are prevented from entering into the supply space 39a at the time of switching from the supply of the dispersion 55 to the supply of the cleaning liquid.

After the supply of the cleaning liquid and/or the dispersion 55 is stopped, detection of ID pattern and detection of fluorescent light can be carried out in the same "testing procedure" as in the test cell 1 in the first embodiment above. In the test cell 2 in the second embodiment, also, the microbeads 7 are prevented from overlapping each other; therefore, all the microbeads 7 present in the imaging region can be imaged, and the target substance(s) can be analyzed with high accuracy.

During or after the supply of the dispersion 55 and the cleaning liquid and before the start of imaging of the microbeads 7, it is preferable that vibration, agitation, turbulence or the like is generated continuously or intermittently so as to prevent clogging with the microbeads 7. A testing apparatus constructed by assembling a clogging preventive means and the test cell 2 will be described below.

Figure 14:
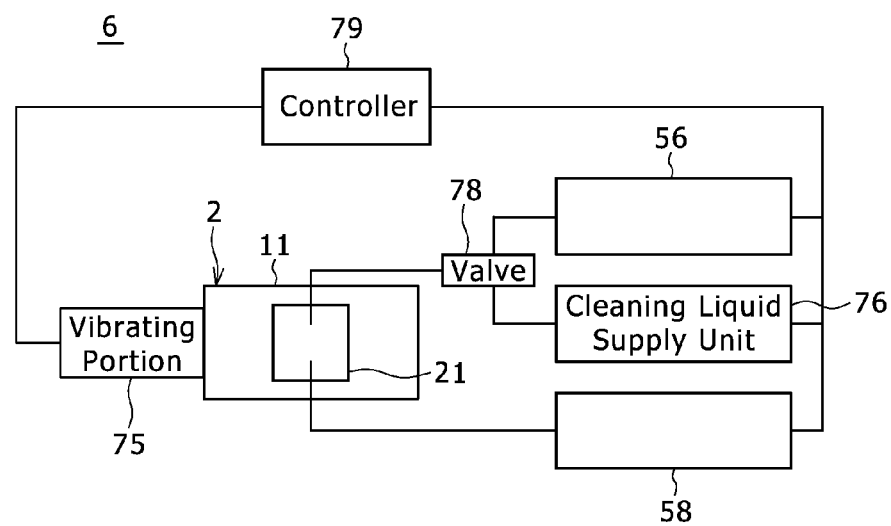
FIG. 14 is a block diagram of an example of a testing apparatus.

FIG. 14 is a block diagram of an example of a testing apparatus 6. The testing apparatus 6 has a controller 79 and a vibrating portion 75. In the condition where the test cell 2 is mounted into the testing apparatus 6, the vibrating portion 75 is in contact with the test cell 2, and the controller 79 is in connection to the supply unit 56 and the discharge unit 58.

The controller 79 sends control signals to the pressure control portion (the pressuring means, the pressure reducing portion) of the supply unit 56 and the discharge unit 58, and starts or stops the supply of the dispersion 55. A detector for liquid feed pressure may be disposed in a flow channel (the pipings 51, 52, etc.) in the course from the supply unit 56 to the discharge unit 58. In that case, the controller 79 determines the control signals to the pressure control portion on the basis of a detection signal from the detector, whereby a liquid feed quantity and a liquid feed rate for the dispersion 55 can be maintained at predetermined values.

The testing apparatus 6 may be provided with a cleaning liquid supply unit 76. In this case, a switching portion 78 such as a change-over valve is provided between the cleaning liquid supply unit 76 and the test cell 2 and between the supply unit 56 of the dispersion 55 and the test cell 2. The controller 79 changes over the switching portion 78 at a preset timing, to change the kind of liquid that is fed to the test cell 2.

The vibrating portion 75 has a vibrating element such as an eccentric motor, a piezoelectric element, a voice coil motor, an ultrasonic vibrating element, etc. The controller 79 puts the vibrating element into vibration during the supply of the dispersion 55 and/or the cleaning liquid or after the supply is stopped. The vibrating portion 75 is in contact with a part or the whole part of the test cell 2, either directly or indirectly.

A vibrational force is transmitted to the test cell 2, whereby agitation or turbulence is induced in the dispersion 55 in the containing space 39 and/or the dispersion 55 flowing toward the containing space 39. By the agitation or turbulence, precipitation of the microbeads 7 and clogging with the microbeads 7 are prevented. Accordingly, the probability of the microbeads 7 reaching the imaging region is enhanced.

Incidentally, agitation or turbulence of the dispersion 55 may be generated by other means than the vibrating portion 75. For example, the agitation or turbulence may be generated by a method in which either one or both of the pressurizing portion in the supply unit 56 and the pressure reducing portion in the discharge unit 58 are controlled by the controller 79 so as to control the feed of the dispersion 55. Specifically, the pressure difference produced by the pressure control portion is controlled so as to feed the dispersion intermittently (in a pulsed manner), whereby the agitation or turbulence can be generated.

When this testing apparatus 6 is combined with a fluorescent light detection device and an image pick-up device, all of the steps including the containment of the microbeads 7, the washing (cleaning) of the microbeads 7, the identification of the ID pattern(s), and the detection of the fluorescent light can be performed automatically. Besides, by replacing the test cell 2, the testing apparatus 6 can be repeatedly used also for different cells.

Figure 15:
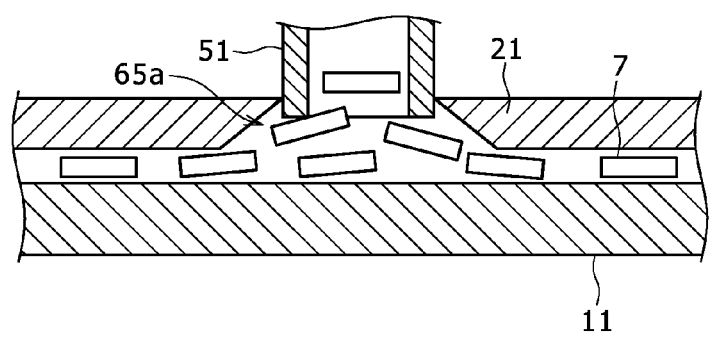
FIG. 15 is an enlarged sectional view illustrating an example of a supply port.

Incidentally, in the test cells 1 and 2 in the first and second embodiments above, if the supply port 65a (the through-hole 25) is constant in diameter from the face-side surface to the back surface of the cover 21 or is decreased in diameter (reversely tapered) toward the containing space 39, the microbeads 7 are more liable to be caught on the corner portion at the lower end of the supply port 65a, with the result of clogging with the microbeads 7. In view of this, it is preferable that the supply port 65a (the through-hole 25) is so tapered that its diameter is increased toward the containing space 39 as shown in FIG. 15.

Either one or both of the support substrate 11 and the cover 21 may be subjected to a surface treatment. Examples of the surface treatment include a surface treatment for suppressing nonspecific adsorption of the microbeads 7, and a hydrophilicity- or hydrophobicity-imparting or enhancing treatment for achieving smoother introduction of the dispersion. Especially, in the case where the liquid phase of the dispersion 55 is water or a hydrophilic solvent, a hydrophilicity-imparting or enhancing treatment of the surfaces constituting the inner walls of the passage for the dispersion (the inner wall surfaces of the pipings 51, 52, the surface of the cover 21, and the surface of the support substrate 11) facilitates the introduction of the dispersion 55.

The test cell 1 according to embodiments of the present application ensures that microbeads 7 are prevented from overlapping each other and that the fluorescent light coming, for example, from a fluorescent substance used to label a target substance can be detected with high accuracy. Therefore, the test cell 1 is capable of contributing to further enhancement of throughput and speed of various biochemical analyses in which microbeads are used.

It should be understood that various changes and modifications to the presently preferred embodiments described herein will be apparent to those skilled in the art. Such changes and modifications can be made without departing from the spirit and scope and without diminishing its intended advantages. It is therefore intended that such changes and modifications be covered by the appended claims.

The invention claimed is:

1. A cell for testing microbeads, used for testing microbeads each formed in a cylindrical shape having an upper surface and a lower surface opposite to and substantially parallel to each other and a side surface continuous with the upper and lower surfaces, at least one of the upper surface and the lower surface being provided with an identification pattern, the cell comprising:
    a support substrate; and
    a cover disposed opposite to the support substrate, wherein
    a space between the support substrate and the cover forms a containing space in which to dispose the microbeads, and
    the distance between the support substrate and the cover is greater than a thickness of the microbeads and smaller than twice the thickness of the microbeads; and
    wherein at least one of the support substrate and the cover are provided with a pillar, the height of the pillar is greater than the thickness of the microbeads and smaller than twice the thickness of the microbeads, and
    the pillar is provided with a cutout smaller than at least one of the diameter of the upper surface of the microbead and the diameter of the lower surface of the microbead.

2. The cell for testing microbeads according to claim 1, wherein
    the pillar is so formed as to surround the containing space, and
    the cover is formed with a through-hole through which the containing space and the external space are connected to each other.

3. The cell for testing microbeads according to claim 2, comprising an absorbing member disposed to face the cutout.

4. The cell for testing microbeads according to claim 3, wherein
    the support substrate is formed with a mount part where that portion of the support substrate which faces the containing space is projected to be higher than the other portion, and
    the absorbing member is disposed at an edge part lower than the mount part of the support substrate.

5. The cell for testing microbeads according to claim 1, wherein
the cell includes a supply port and a discharge port through which the containing space and the external space are connected to each other,
the pillar is located between the supply port and the discharge port, and
the pillar partitions the containing space into a supply space on the supply port side and a discharge space on the discharge port side.

6. The cell for testing microbeads according to claim 5, wherein the supply space has a swollen part swelled toward the discharge port.

7. The cell for testing microbeads according to claim 1, wherein a reflecting mirror is disposed at least at a part of that portion of the support substrate which faces the containing space.

8. A method of analyzing microbeads each formed in a cylindrical shape having an upper surface and a lower surface opposite to and substantially parallel to each other and a side surface continuous with the upper and lower surfaces, at least one of the upper surface and the lower surface being provided with an identification pattern, the method comprising:
a containing step of disposing a support substrate and a cover opposite to each other with a distance therebetween greater than a thickness of the microbeads and smaller than twice the thickness of the microbeads, and disposing the microbeads in a containing space between the support substrate and the cover; and
an imaging step of imaging the microbeads present in the containing space; and
wherein the containing step includes connecting the containing space to a supply unit and a discharge unit, generating a pressure difference between the supply unit and the discharge unit, and sucking into the containing space a dispersion in which the microbeads are dispersed.

9. The method of analyzing microbeads according to claim 8, wherein the containing step includes transmitting a vibrational force to a flow channel between the supply unit and the discharge unit so as to agitate the dispersion.

* * * * *